United States Patent [19]

Kodama et al.

[11] Patent Number: 4,542,021
[45] Date of Patent: Sep. 17, 1985

[54] ANTITUMOR COMPOSITIONS FOR NON-INJECTION ADMINISTRATION

[75] Inventors: Kenjiro Kodama; Akira Kuninaka, both of Choshi; Mineo Saneyoshi, 2-102 Chuo Daini Koumuin Shukusha, Kita 7 Jo Nishi 9-Chome, Kita-Ku, Sapporo-Shi, Hokkaido, all of Japan

[73] Assignees: Yamasa Shoyu Kabushiki Kaisha, Chiba; Mineo Saneyoshi, Hokkaido, both of Japan

[21] Appl. No.: 205,592

[22] Filed: Nov. 10, 1980

Related U.S. Application Data

[63] Continuation of Ser. No. 49,635, Jun. 18, 1979, abandoned.

[30] Foreign Application Priority Data

Jun. 20, 1978 [JP] Japan .................................. 53-73698

[51] Int. Cl.⁴ ...................... H61K 31/71; H61K 31/70
[52] U.S. Cl. ...................................... 514/49; 514/908; 514/966
[58] Field of Search .............................. 424/181, 180

[56] References Cited

PUBLICATIONS

Chemical Abstracts 88: 23342u (1978) Abstracting Japan Kokai 7789,681, Published Jul. 27, 1977.

Primary Examiner—Jerome D. Goldberg
Attorney, Agent, or Firm—Wenderoth, Lind & Ponack

[57] ABSTRACT

An antitumor composition comprising a pharmacologically effective quantity of an ester of 1-β-D-arabinofuranosylcytosine-5'-phosphate represented by the general formula

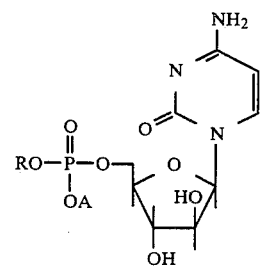

where R is a monovalent aliphatic hydrocarbon group having 14 to 23 carbon atoms, and A designates a hydrogen atom or a pharmaceutically-acceptable alkali cation, and a vehicle is effective when administered by a non-injection method, particularly orally.

5 Claims, No Drawings

ANTITUMOR COMPOSITIONS FOR NON-INJECTION ADMINISTRATION

This application is a continuation of application Ser. No. 49,635, filed June 18, 1979 (now abandoned).

BACKGROUND OF THE INVENTION

1. Field of the Invention

This invention relates to novel antitumor compositions which exhibit marked antitumor action by non-injection administration. More specifically, the invention relates to novel antitumor compositions for non-injection administration each of which comprises a pharmacologically effective quantity of an ester of 1-β-D-arabinofuranosylcytosine-5'-phosphate and a vehicle.

2. Prior Art

It has been known that 1-β-D-arabinofuranosyl cytosine (hereinafter referred to as ara-C) is an agent which is indispensable for chemotherapy of cancers, especially leukemias such as acute lymphatic leukemia (ALL), acute myelogenous leukemia (AML) and meningo-leukemia. Recently, ara-C has been often employed in combination with other agents, for example, in DCMP (daunomycin-ara-C-mitomycin-predonisolone) therapy and MFC (mitomycin-5-fluorouracil-ara-C) therapy. Thus, the ara-C has been often used as an essential agent of combined therapeutics in the chemotherapy of leukemias as well as solid cancers such as lymphoma, gastric and intestinal cancers and adenocarcinoma (e.g., reference is made to "Chemotherapeutics of Cancers", Yakuzai Koza Vol. 1, p.p. 75–80, compiled by H. Niitani and H. Kanagami, published by Clinic Magazine Company, Japan, July 1, 1977). At the moment, however, ara-C can only be used for intravenous or intramuscular injection from a viewpoint of pharmacodynamics and actually cannot be used for oral administration. This fact has been an obstacle to further extensive applications of ara-C. Especially, its continuous administration by intravenous injection gives rise to physical and mental pain to a considerable extent in the patients. Thus, the development of forms of ara-C which can be administered orally has been urgently needed in the clinical field.

Hitherto, the syntheses of ara-C derivatives which can be administered orally have been tried (cf. J. Med. Chem. Vol. 19, No. 8, p.p. 1013–1016, 1976). It has also been reported that the oral administration of ara-C is effective in combination with a cytidinedeaminase inhibitor such as tetrahydrouridine (cf. Cancer Research, Vol. 30, p.p. 2166–2172, 1970). However, the effects are not remarkable and there has been no prospect of practical use of this administration.

On the other hand, the present inventors have synthesized alkyl or aryl esters of arabinofuranosylcytosine-5'-phosphate (hereinafter referred to as ara-CMP) in order to study improvement in so-called bioavailability of the ara-C derivatives such as their resistivity to cytidinedeaminase, their effects on ara-C-resistant strains, and their antitumor properties based on selective affinity for organs. These esters were tested with respect to their antitumor properties (cf. Reports on the proceedings of the 35th annual meeting of the Japanese Cancer Association, p. 133, No. 476, issued by Nippon Gan Gakkai, Sept. 1, 1976). The esters of ara-CMP, however, only showed a lower activity than ara-C and ara-CMP in cell proliferation-inhibition effects in vitro using L5178Y cells. Also, in the antitumor tests in vivo using mouse-leukemia cell L1210, the esters tested only showed an increase in life span similar to or lower than ara-CMP when they were administered intraperitoneally. The alkyl esters having 11 or more carbon atoms in the alkyl moiety showed some effectiveness in that the effective doses were decreased but were accompanied by an increase in toxicity. On the whole, in both in vitro experiment and intraperitoneal administration, pharmacologically useful improvements in ara-C or ara-CMP were not observed over the ara-CMP esters.

Hitherto, it has been considered that the most effective administration of a drug is generally attained by intravenous injection (or intraperitoneal injection), and the maintenance of the drug concentration in the blood at a certain level is required for the drug to exhibit effectiveness in the therapy of leukemias such as L1210 leukemia. Consequently, the ara-CMP esters which are not very effective in intraperitoneal administration have not especially been appreciated as antitumor agents.

SUMMARY OF THE INVENTION

The present inventors have carried out extensive research on the derivatives of ara-C in order to develop novel dosage forms of ara-C which will exhibit marked antitumor properties in non-injection administration such as oral administration. The present invention is based on the finding that ara-CMP esters, which have shown no significant effectiveness by parenteral administration, unexpectedly exhibit extremely strong antitumor properties by non-injection administration. According to the present invention, briefly summarized, there are provided antitumor compositions for non-injection administration each comprising a pharmacologically effective quantity of an ester of 1-β-D-arabinofuranosylcytosine-5'-phosphate represented by the following formula and a vehicle.

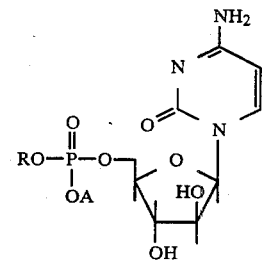

wherein R is a monovalent aliphatic hydrocarbon group having 14 to 23 carbon atoms, and A stands for a hydrogen atom or a pharmaceutically-acceptable alkali cation.

DETAILED DESCRIPTION OF THE INVENTION

The ara-CMP esters, the active component of the present antitumor compositions, are the series of the compounds represented by the above general formula. The substituent R in the formula means a monovalent aliphatic hydrocarbon group having 14 to 23 carbon atoms, which may be saturated or unsaturated and can be branched or substituted with a suitable functional group provided that their effects are equivalent. The symbol A stands for hydrogen atom or a pharmaceutically-acceptable alkali cation, examples of which are alkali metals such as sodium and potassium, alkaline earth metals such as calcium and magnesium, and ammonium ion.

Examples of the ara-CMP esters are ara-CMP-tetradecyl ester (hereinafter referred to as C14-ara-CMP ester), ara-CMP-pentadecyl ester (hereinafter referred to as C15-ara-CMP ester), ara-CMP-cetyl ester (hereinafter referred to as C16-ara-CMP ester), ara-CMP-heptadecyl ester (hereinafter referred to as C17-ara-CMP ester), ara-CMP-stearyl ester (hereinafter referred to as C18-ara-CMP ester), ara-CMP-nonadecyl ester (hereinafter referred to as C19-ara-CMP ester), ara-CMP-eicosyl ester (hereinafter referred to as C20-ara CMP ester), ara-CMP-heneicosyl ester (hereinafter referred to as C21-ara-CMP ester), ara-CMP-tricosyl ester (hereinafter referred to as C23-ara-CMP ester), ara-CMP-oleyl ester (hereinafter referred to as C18-1-ara-CMP ester), ara-CMP linoleyl ester, ara-CMP palmitoleyl ester, and the alkali salts thereof. Among them C16-ara-CMP ester, C18-ara-CMP ester, C18-1-ara-CMP ester and C20-ara-CMP ester and alkali salts thereof are preferable.

The process for preparing the ara-CMP esters is not especially restricted in the present invention. One of the representative processes for the preparation is, for example, to mix (A) the ara-CMP salt which has been protected at its $N^4-$, $O^{2'}-$ and/or $O^{3'}-$ positions with an acyl group (e.g., acetyl, butyryl, benzoyl groups) and (B) an alcohol having the desired monovalent aliphatic hydrocarbon group, to condense. The condensation reaction is accelerated by an aryl-sulfonyl chloride in an organic solvent or mixed organic solvents (as disclosed in the specification of Japanese Laid-Open Pat. No. 89681/1977).

Examples of the ara-CMP salts in the above mentioned process are tertiary alkylammonium salts such as triethylammonium salt, tri-n-butylammonium salt, tri-n-octylammonium salt, quaternary alkylammonium hydroxide salts such as methyl-tri-n-butylammonium hydroxide salt, methyl-tri-n-octylammonium hydroxide salt, and amidine salts such as 4-morpholino-N,N'-dicyclohexylcarboxamidine salt. Examples of the organic solvents are N,N-dimethylformamide, N,N-dimethylacetamide, chloroform, pyridine, dioxane, tetrahydrofuran, ethyl acetate, tri-n-butylamine, and mixtures thereof. Examples of the arylsulfonyl chlorides are tri-isopropylbenzenesulfonyl chloride, o-tosyl chloride, p-tosyl chloride, benzenesulfonyl chloride, 2-mesitylenesulfonyl chloride, and the like.

The reaction conditions are, for example, in pyridine, 1 to 2 hours at room temperature when p-tosyl chloride is used as the condensation agent, and 1 to 20 hours at room temperature when tri-isopropyl-benzenesulfonyl chloride is used.

Each of the antitumor compositions of the present invention contains a pharmacologically effective quantity of the ara-CMP ester and a vehicle and is prepared into a dosage form which is suitable for non-injection administrations. The dosage forms for non-injection uses include, depending on the methods and routes of administration, oral preparations such as tablets, capsules, soft capsules, granules, slow-releasing granules, fine granules, powders and syrups; parenteral preparations such as suppositories; and local preparations such as ointments.

Suitable vehicles to be employed for making oral preparations are, for example, lactose, sucrose, starch, talc, magnesium stearate, crystalline cellulose, methylcellulose, carboxymethylcellulose, glycerine, sodium alginate, and gum arabic. As the coating materials for slow-releasing granules, ETHOCEL (trade name, supplied from The Dow Chemical Company, USA), EUDRAGIT (trade name, supplied from Rohm & Haas Company, USA), etc. can be used. As the vehicles for soft capsules, for example, edible oils and fats having a melting point of lower than about 40° C. such as sesame oil, rape seed oil, fatty oils having middle-length carbon chains are used and, if desired, surface active agents, suspending agents and/or silicon dioxide can be added thereto.

Depending on the dosage forms of the pharmaceutical preparations, varieties of binders, disintegrators, lubricants, preservatives, flavoring agents, coloring agents, seasoning agents and the like can be suitably selected and incorporated into the preparations. The pharmaceutical preparations can be prepared according to conventional methods. The pharmacologically-effecitve quantity of the ara-CMP esters in the oral preparations depends upon the kind of the esters, and their daily doses for adult are generally in the range of 30 to 1500 mg (0.5 to 25 mg/kg of body weight). The preferable dosage of the pharmaceutical preparation unit depends on the kind of ara-CMP esters, the dosage forms, and the schedules of administration and is generally in the range of 5 to 500 mg. In each dose of the pharmaceutical preparations, the ester comprises approximately 0.5% by weight or more of the dose.

The base materials for the suppositories are not especially restricted, and conventional base materials such as cacao butter, emulsified cacao butter, laurin fat, and WITEPSOL are used. The suppositories are prepared according to conventional methods. The pharmacologically-effective quantity of an ara-CMP ester in suppositories depends upon the kind of the ester, and its daily dose is generally in the range of 30 to 1500 mg (0.5 to 25 mg/kg of body weight). The dosage of the preparation unit is preferably in the range of 15 to 750 mg.

As the base for ointments to be applied locally, for example, greasy base materials such as liquid paraffin, cetyl alcohol, stearyl alcohol, white vaseline, squalan, lanolin, and cholesterol can be used. A suitable concentration of an ara-CMP ester in the ointments depends on the kind of the ester and is generally in the range of 0.3 to 10% by weight.

The pharmacological activity tests and acute toxicity tests of the ara-CMP esters are described below.

TEST EXAMPLE 1

Therapeutic Test on L1210 Leukemia

The L1210 leukemic cell suspension ($1 \times 10^5$ cells/0.2 ml) was implanted intraperitoneally in $BDF_1$ mice (males, 18 to 22 g, females, 16 to 20 g) (7 mice per group). From 24 hours after the implantation to the 5th day thereafter, the predetermined doses of the compounds to be tested were orally administered to the mice consecutively once a day. The compounds to be tested were dissolved or suspended in a phosphate-buffered salt solution (PBS) containing 0.5% carboxymethylcellulose, and given at a dose rate of 0.1 ml per 10 g of each mouse's body weight. To a control group, only the same solvent as used for the dissolution of the compounds to be tested was administered in the same way. The mean survival times (MST) for each group were calculated, and the corresponding increase in life span (%ILS) was obtained in accordance with the following formula, the results of which are shown in Table 1.

$$\%ILS = \left( \frac{MST \text{ of the treated group}}{MST \text{ of the control group}} - 1 \right) \times 100$$

TABLE 1

| Tested compound | % ILS at dose (mg/kg/day) of | | | | | | |
|---|---|---|---|---|---|---|---|
| | 6.25 | 12.5 | 25 | 50 | 100 | 200 | 400 |
| ara-C (hydrochloride) | | | | | 22 | 34 | 67 |
| ara-CMP | | | | 8 | 21 | 57 | 73 |
| ara-CMP methyl ester | | | | | 13 | 48 | 65 |
| ara-CMP decyl ester | | | 0 | 4 | 8 | 36 | 39 |
| ara-CMP undecyl ester | | | 12 | 27 | 31 | 78 | |
| C14-ara-CMP ester | | | | 62 | 88 | 105 | 134 |
| C15-ara-CMP ester | | | | 70 | 95 | 135 | |
| C16-ara-CMP ester | | 19 | 30 | 73 | 88 | 137 | >227[1] |
| C17-ara-CMP ester | 11 | 32 | 52 | 87 | 123 | >154 | −15 |
| C18-ara-CMP ester | 46 | 52 | 69 | 114 | >200 | 53 | −7 |
| C18-1-ara-CMP ester | 20 | 39 | 54 | 81 | 109 | 120 | >159 |
| C20-ara-CMP ester | 19 | 39 | 60 | 90 | 126 | >199 | |
| C23-ara-CMP ester | | 29 | 51 | 65 | 81 | 110 | 128 |
| ara-CMP hexacosyl ester | | | 14 | 23 | 27 | 52 | 86 |

Note:
[1]The symbol (>) means that some mice survived the test period (30 days).

TEST EXAMPLE 2

Effectiveness against B16 Melanoma

The B16 melanoma cells ($1 \times 10^6$ cells) were implanted to the right side-abdominal hypoderms of $BDF_1$ mice (male, 18 to 22 g). From the 13th day after the implantation to death the compounds to be tested were administered orally 3 times a week. The compounds to be tested were dissolved in a phosphate-buffered salt solution (PBS) containing 0.5% carboxymethyl-cellulose to a suitable concentration, and given to the mice at a dose rate of 0.1 ml per 10 g of each mouse's body weight. The increases in life span (%ILS) were calculated in accordance with the same formula as described in Test Example 1. The results are shown in Table 2.

TABLE 2

| Tested compound | Dose (mg/kg) | Mean survival time (MST ± SE) | Increase in life span (% ILS) |
|---|---|---|---|
| Control | — | 22.0 ± 2.19 | — |
| ara-C (hydrochloride) | 100 | 26.8 ± 1.50 | 22 |
| | 200 | 21.0 ± 1.76 | −5 |
| | 400 | 22.2 ± 2.82 | 1 |
| 5-fluorouracil | 25 | 22.0 ± 1.45 | 0 |
| | 50 | 25.0 ± 2.26 | 14 |
| | 100 | 19.6 ± 0.98 | −11 |
| C18-ara-CMP ester | 50 | 30.0 ± 1.30 | 36* |
| | 100 | 25.8 ± 1.98 | 17 |
| | 200 | 26.8 ± 2.20 | 22 |

*level of significance at 0.05% or lower.

TEST EXAMPLE 3

Effectiveness against experimental tumor proliferation models in the lymph nodes L1210 leukemic cells ($1 \times 10^6$ cells/0.05 ml) were implanted to the right inner-thigh hypoderms of $BDF_1$ mice (males, 18 to 22 g). From one day after the transplantation, the compounds to be tested were administered intraperitoneally or orally to the mice once a day consecutively for 6 days. The compounds being tested were dissolved in a phosphate-buffered salt solution (PBS) containing 0.5% carboxymethylcellulose to a suitable concentration, and administered to the mice at a dose rate of 0.1 ml per 10 g of each mouse's body weight. The increases in life span (%ILS) were calculated similarly as in Test Example 1. The results are shown in Table 3.

TABLE 3

| Tested compound | Dose (mg/kg/day) | Route of administration | Mean survival time (MST ± SE) | Increase in life span (% ILS) |
|---|---|---|---|---|
| Control | — | ip | 6.9 ± 0.18 | — |
| ara-C (hydrochloride) | 50 | ip | 13.9 ± 0.59 | 101 |
| | 100 | ip | 14.5 ± 0.62 | 110 |
| C18-ara-CMP ester | 25 | ip | 17.4 ± 0.40 | 152 |
| | 50 | ip | 20.2 ± 0.53 | 193 |
| | 50 | po | 18.3 ± 0.62 | 165 |
| | 100 | po | 19.9 ± 0.48 | 188 |

Furthermore, in a similar manner, each of the test compounds was administered only once on the sixth day after implantation. As the result, anti-tumor effectivenesses as indicated in Table 4 were exhibited.

TABLE 4

| Tested compound | Dose (mg/kg) | Route of administration | Mean survival Time (MST ± SE) | Increase in life span (% ILS) |
|---|---|---|---|---|
| Control | | | 7.3 ± 0.16 | — |
| ara-C (hydrochloride) | 250 | ip | 9.9 ± 0.13 | 36 |
| | 500 | ip | 10.9 ± 0.23 | 49 |
| C18-ara-CMP ester | 250 | po | 14.0 ± 0.53 | 92 |
| | 500 | po | 17.3 ± 0.49 | 137 |

TEST EXAMPLE 4

Acute toxicity test

The C18-ara-CMP ester was dissolved in saline containing 0.5% carboxymethylcellulose, and given orally to ICR-JCL mice (males, 24 to 26 g) at a dose rate of 0.2 ml per 10 g of each mouse's body weight. The mice thus treated were observed for 7 days. The $LD_{50}$ value was;

$LD_{50}$ (po) 1400(1283–1517) mg/kg (reliability limit 95%).

The C18-ara-CMP ester dissolved in saline was administered intraperitoneally to ICR-JCL mice (males, 24 to 26 g) at a dose rate of 0.2 ml per 10 g of each mouse's body weight. The $LD_{50}$ value obtained on the 7th day was;

$LD_{50}$ (ip) 137(131–143) mg/kg (reliability limit 95%).

TEST EXAMPLE 5

Acute toxicity test

An ara-CMP ester was neutralized and dissolved in saline containing 0.5% of carboxymethylcellulose, and the resulting solution was orally administered to ICR-JCL mice (males, 24 to 26 g) in a dose of 0.2 ml per 10 g of each mouse's body weight. The $LD_{50}$ values calculated on the 14th day after the administration were as set forth in Table 5.

TABLE 5

| ara-CMP ester | $LD_{50}$ value | |
|---|---|---|
| C16-ara-CMP ester | 2190 mg/kg | (2056–2324*) |
| C18-ara-CMP ester | 1050 | (981–1919) |
| C18-1-ara-CMP ester | 3750 | (2990–4510) |
| C20-ara-CMP ester | 2720 | (2550–2890) |

*95% reliability limit

Examples of production of the ara-CMP esters which are the effective components of the present antitumor compositions as well as the examples of preparation for the present antitumor compositions will now be described.

PRODUCTION EXAMPLE 1

10 ml of pyridine were added to 10 m mol of $N^4$, $O^{2'}$, $O^{3'}$-triacetyl ara-CMP (tri-n-butylammonium)salt and 5.4 g (20 m mol) of stearyl alcohol to dissolve them, and then 3.8 g (20 m mol) of p-tosyl chloride was further added thereto. The mixture was caused to react. After 2 hours, 100 ml of water and 50 ml of chloroform were added to the reaction mixture, which was then shaken. The resulting chloroform layer was taken out and 20 ml of ammonia water and 50 ml of ethanol were added thereto to prepare a homogeneous solution. The resulting solution was allowed to stand overnight, and then water was added thereto with stirring, the reaction product thereby being extrated into the water layer. The resulting aqueous solution was adjusted to a pH of 2.0 to 2.5 with concentrated hydrochloric acid to separate out the product (free acid). The separated product was collected by filtration and water was added thereto. The mixture thus obtained was adjusted with sodium hydroxide to a pH of 7 to 8. The resulting solution was again adjusted to a pH of 2.0 to 2.5 with hydrochloric acid to separate out the objective free acid. The separated free acid was collected by filtration, suspended in ethanol and stirred, filtered, and dried to obtain 4.3 g (yield 74.7%) of C18-ara-CMP ester.

Elementary analysis: as $C_{27}H_{50}N_3O_8P$. Calculated: $P$ (%)=5.38; Found: $P$ (%)=5.23.

Melting point: 224°–226° C. (decomposed) (free acid); 203°–205° C. (decomposed) (sodium salt).

Thin-layer chromatography: (developing solvent: ethanol:n-butanol:1M ammonium acetate (pH 7.5)=2:5:3); $Rf$=0.79.

PRODUCTION EXAMPLE 2

The process of the preceding Example 1 was employed for various kinds of alcohols in suitable quantities to produce the corresponding ara-CMP esters. The results and the properties of the resulting esters are shown in Table 6.

TABLE 6

| Compounds produced | Alcohols kinds | g | m.mol | Yield g | Yield % | Molecular formula | Elementary analysis P (%) calculated | Elementary analysis P (%) found | Melting point °C. (decomposed) free acid | Melting point °C. (decomposed) sodium salt | Thin layer chromatography Rf |
|---|---|---|---|---|---|---|---|---|---|---|---|
| C14-ara-CMP ester | tetradecanol | 6.4 | 30 | 4.0 | 77.0 | $C_{23}H_{42}N_3O_8P$ | 5.96 | 5.74 | 225–227 | 216–218 | 0.75 |
| C15-ara-CMP ester | pentadecanol | 6.8 | " | 4.5 | 84.3 | $C_{24}H_{44}N_3O_8P$ | 5.80 | 5.69 | 221–223 | 197–199 | 0.76 |
| C16-ara-CMP ester | cetyl alcohol | 7.3 | " | 4.5 | 82.1 | $C_{25}H_{46}N_3O_8P$ | 5.66 | 5.40 | 226–228 | | 0.77 |
| C17-ara-CMP ester | heptadecanol | 5.1 | 20 | 4.5 | 80.1 | $C_{26}H_{48}N_3O_8P$ | 5.52 | 5.22 | 219–221 | 201–203 | 0.78 |
| C18-1-ara-CMP ester | oleyl alcohol | 5.4 | " | 4.5 | 78.4 | $C_{27}H_{48}N_3O_8P$ | 5.40 | 5.19 | 218–220 | 203–205 | 0.80 |
| C20-ara-CMP ester | eicosanol | 6.0 | " | 4.7 | 77.8 | $C_{29}H_{54}N_3O_8P$ | 5.13 | 4.85 | 216–218 | 191–193 | 0.80 |
| C23-ara-CMP ester | tricosanol | 4.0 | 11.7 | 3.6 | 55.7 | $C_{32}H_{60}N_3O_8P$ | 5.80 | 4.73 | 217–219 | 204–206 | 0.80 |

PREPARATION EXAMPLE 1

A mixture consisting of 10 g of pulverized C18-ara-CAMP ester, 50 g of crystalline cellulose, 3 g of magnesium stearate, 100 g of lactose, and 100 g of potato starch is blended and capsuled, each capsule containing 263 mg of the composition.

PREPARATION EXAMPLE 2

A mixture consisting of 40 g of pulverized C16-ara-CMP ester (sodium salt), 100 g of crystalline cellulose, 6 g of magnesium stearate, and 94 g of lactose is blended and capsuled, each capsule containing 240 mg of the composition.

PREPARATION EXAMPLE 3

A mixture consisting of 20 g of C20-ara-CMP ester, 176 g of crystalline cellulose, 12 g of magnesium stearate, and 40 g of calcium salt of carboxymethyl-cellulose is thoroughly blended and formed into slugs. The resulting slugs are subjected to a granulation treatment by an oscillator equipped with a No. 10 sieve. To the granules is further added 12 g of magnesium stearate, and the resulting material is formed into tablets, each tablet containing 260 mg of the composition. The resulting uncoated tablets are then provided with sugar coating or film coating.

PREPARATION EXAMPLE 4

A mixture consisting of 200 g of C18-1-ara-CMP ester, 5 kg of maize starch, 4 kg of lactose, and 3 kg of sucrose is blended in a fluid-coating apparatus. The resulting fluidized powder is granulated by spraying into the fluidized powder a solution which has been prepared by dissolving 200 g of carboxymethyl-cellulose sodium salt in 15 liters of 30% methanol. After drying, the resulting granules are subjected to a uniforming treatment and formed into preparations which contain 20 mg of C18-1-ara-CMP ester per 1 g of the fine granules.

PREPARATION EXAMPLE 5

A mixture of 200 g of C18-1-ara-CMP (sodium salt) and 4.8 kg of a middle-length chain fatty acid triglyceride is homogeneously blended and is prepared into soft capsules by means of a soft capsule filler, each capsule containing 20 mg of C18-1-ara-CMP (sodium salt).

PREPARATION EXAMPLE 6

A mixture of 2.5 kg of lactose, 1.45 kg of starch, and 100 g of C18-ara-CMP ester is thoroughly blended and is then subjected to a wet granulation treatment with addition of 500 ml of an alcohol solution containing 10% hydroxypropylcellulose. After drying and uniforming, the resulting granules are sprayed with a 1:1 mixed solution of methylene chloride and normal hexane containing 10% Ethocel (ethylcellulose supplied from Dow Chemical Company), to prepare slow-releasing granules.

PREPARATION EXAMPLE 7

About 1.4 kg of WITEPSOL W35 (trade name, supplied from Dynamit Nobel Company, Germany) is heated to 60° C. and melted, and 120 g of C18-ara-CMP ester is added thereto. The mixture is then homogeneously blended. The blended mixture is cooled to 40° C. A specific amount of the mixture is then poured into each of a number of tiny plastic containers by means of a suppository filler, and the filled plastic containers are sealed to prepare suppositories.

PREPARATION EXAMPLE 8

A mixture of 100 g of fluid paraffin, 50 g of cetyl alcohol, and 790 g of vaseline is thoroughly blended with heating to 80° C. Then, 3 g of cholesterol and 50 g of C16-ara-CMP ester are added thereto, after which the mixture is stirred. The resulting mixture is allowed to stand at room temperature to obtain an ointment.

PREPARATION EXAMPLE 9

A mixture consisting of 20 g of C18-1-ara-CMP ester, 100 g of potato starch, 70 g of lactose, 10 g of crystalline cellulose, and 1.0 g of magnesium stearate is blended and is then capsuled, each capsule containing 201 mg of the composition.

PREPARATION EXAMPLE 10

The various preparations of the ara-CMP esters are designed and shown in the following Table 7.

TABLE 7

| ara-CMP esters | Daily doses (/60 kg of body weight) | Doses per preparation unit | |
|---|---|---|---|
| | | oral preparations | suppositories |
| C18-ara-CMP ester | 30–300 mg | 5–100 mg | 15–150 mg |
| C16-ara-CMP ester | 120–1200 mg | 20–400 mg | 60–600 mg |
| C18-1-ara-CMP ester | 60–600 mg | 10–200 mg | 30–300 mg |
| C20-ara-CMP ester | 60–600 mg | 10–200 mg | 30–300 mg |
| C14-ara-CMP ester | 150–1500 mg | 25–500 mg | 75–750 mg |

What is claimed is:

1. A method of inhibiting the growth of a malignant tumor treatable by ara-C in an animal which comprises administering orall to said animal a pharmacologically effective quantity sufficient to inhibit malignant tumors treatable by ara-C of an ester of 1-$\beta$-D-arabinofuranosylcytosine-5'-phosphate represented by the formula

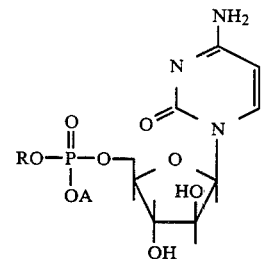

wherein R is a monovalent aliphatic hydrocarbon group having 14 to 23 carbon atoms selected from the group consisting of tetradecyl, pentadecyl, cetyl, heptadecyl, stearyl, nonadecyl, eicosyl, heneicosyl, tricosyl, oleyl, linoleyl and palmitoleyl, and A represents a hydrogen atom or a pharmaceutically-acceptable alkali cation.

2. A method according to claim 1, in which said ester is 1-$\beta$-D-arabinofuranosylcytosine-5'-cetylphosphate or a pharmaceutically-acceptable salt thereof.

3. A method according to claim 1 in which said ester is 1-$\beta$-D-arabinofuranosylcytosine-5'-stearylphosphate or a pharmaceutically-acceptable salt thereof.

4. A method according to claim 1 in which said ester is 1-$\beta$-D-arabinofuranosylcytosine-5'-eicosylphosphate or a pharmaceutically-acceptable salt thereof.

5. A method according to claim 1 in which said ester is 1-$\beta$-D-arabinofuranosylcytosine-5'-oleylphosphate or a pharmaceutically-acceptable salt thereof.

* * * * *